United States Patent [19]

Zaiger

[11] Patent Number: Plant 5,474

[45] Date of Patent: May 21, 1985

[54] PEACH TREE (JUNE MAID)

[76] Inventor: Chris F. Zaiger, 537 Rosemore Ave., Modesto, Calif. 95351

[21] Appl. No.: 445,445

[22] Filed: Dec. 13, 1982

[51] Int. Cl.[3] ..... A01H 5/03

[52] U.S. Cl. ..... Plt./43

[58] Field of Search ..... Plt./43

*Primary Examiner*—Robert E. Bagwill

[57] ABSTRACT

A new variety of peach tree which is of large size, vigorous upright growth and a regular productive bearer of large size, yellow flesh, clingstone fruit that have a high degree of red skin color. The fruit is further characterized by its good eating quality and having firm flesh with the ability to ship to long distance markets.

1 Drawing Figure

ORIGIN OF THE VARIETY

The herein variety of peach tree was developed by me in my experimental orchard near Modesto, Calif. as a first generation seedling of a cross between Fayette Peach (Unpatented) and May Grand Nectarine, (U.S. Plant Pat. No. 2,794). The selection was made from a large group of seedlings and maintained under careful and continual observation during which time I recognized its distinct and desirable characteristics and selected the variety for reproduction.

ASEXUAL REPRODUCTION OF THE VARIETY

The present variety of peach tree was asexually reproduced by budding as performed by me in my experimental orchard, located in Modesto, Calif., shows that such reproductions run true to the original tree in all respects.

SUMMARY OF THE VARIETY

My new variety relates to a new and distinct variety of peach tree of large size, with vigorous, upright growth and a regular and heavy bearer of large size early maturing, yellow flesh clingstone fruit having firm flesh with a high degree of red skin color. The fruit ripening and harvested in the same maturity season as Gemfree Peach (U.S. Plant Pat. No. 1,409).

PHOTOGRAPHS OF THE VARIETY

The accompanying photographic illustrations show typical specimens of foliage and fruit of my new peach variety, with upper and lower surfaces of the foliage, an exterior view of the fruit showing shape and skin color, and a fruit divided on its suture plane to reveal flesh coloration and showing the stone remaining in place. The illustrations were taken shortly after being picked at maturity (shipping ripe) and the colors are as nearly true as reasonable possible in a color representation of this type.

DESCRIPTION OF THE VARIETY

The following is a detailed bontanical description of the new and distinct variety of peach tree, its foliage and fruit, based upon observations of specimens grown at Modesto, Calif., with color terminology (except those in common terms) in accordance with Reinhold Color Atlas, by A. Korneruf and J. H. Wanscher.

TREE

Size: Large.
Vigor: Vigorous.
Form: Upright.
Production: Productive.
Density: Medium dense.
Bearing: Regular bearer.

TRUNK

Size: Medium stocky.
Texture: Shaggy.

BRANCHES

Size: Medium stocky.
Lenticels: Medium size. Medium number.
Texture: Smooth to medium rough.

LEAVES

Size Large.
*Average length.*—$7\frac{1}{4}''$.
*Average width.*—$1\frac{3}{4}''$.
Form: Lanceolate.
Margin: Crenate.
Color:
*Upper surface.*—Green (29-F-6) to (29-F-8).
*Lower surface.*—Grayish green (29-E-5) to (29-E-6).
Texture: Smooth.
Petiole: Medium length.
Glands: Small to medium size. Average number 4, alternate, position on base of leaf blade and upper portion of petiole. Reniform.

FLOWER BUDS

Size: Medium size. Medium length.
Form: Plump.
Pubescence: Pubescent.

FLOWERS

Size: Large, showy.
Blooming period Feb. 28, 1980 to Mar. 8, 1980, varies slightly with climatic conditions.

FRUIT

Maturity when described: Hard ripe.
Date of first picking: June 14, 1980.
Date of last picking: June 20, 1980.
Size: Comparatively uniform. Large.

*Average diameter axially.*—$2\frac{7}{8}''$

*Average transversely in suture plane.*—$2\frac{5}{8}''$.

Form: Uniform, nearly globose.

Suture: Distinct, extends from base, discontinues at apex.

Ventral surface: Rounded to slightly lipped.

Cavity: Nearly rounded, slightly elongated in suture plane.

Apex: Rounded to retuse.

SKIN

Thickness: Medium.

Texture: Medium.

Tendency to crack: None.

Down: Moderate.

Color: Bright yellow ground color — (4-A-7) to (5-A-7) overspread with red — (8-B-7) to (9-C-7).

FLESH

Juice: Moderate.

Texture: Firm, meaty.

Ripens: Even.

Flavor: Mild.

Color: Yellow (4-A-6) to dark yellow (4-A-8).

USE

Dessert. Market — local and long distance.

KEEPING QUALITY

Good.

SHIPPING QUALITY

Very Good.

The peach tree and its fruit herein described may vary in slight detail due to climatic and soil conditions under which the variety maybe grown; the present description of that of the variety grown under ecological conditions prevailing at Modesto, Calif.

The following is claimed:

1. A new and distinct variety of peach tree as illustrated and described, which is large size, upright growth and a regular and productive bearer of firm yellow flesh, clingstone fruit with good eating and shipping quality; the fruit is further characterized by having a high degree of attractive red skin color and ripening with Gemfree Peach (U.S. Plant Pat. No. 1,409), but having more consistant production and fewer split pits.

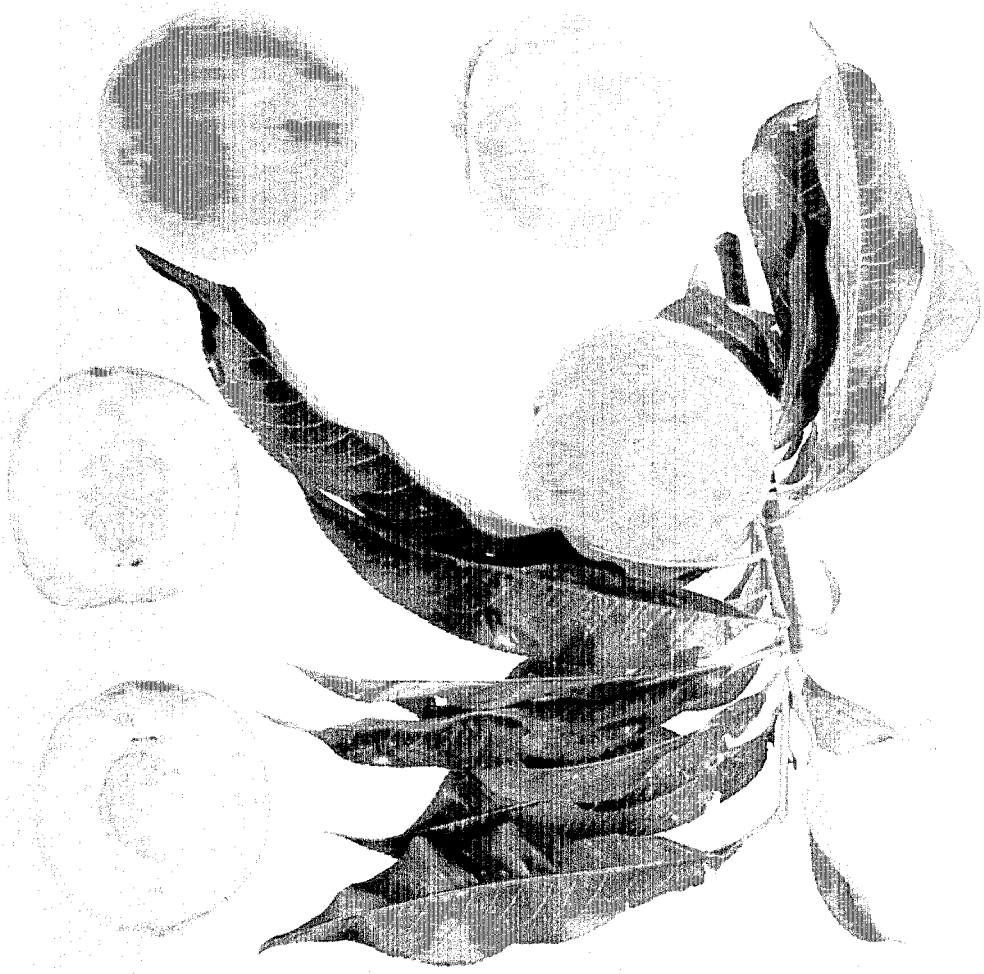

* * * * *